US008715923B2

(12) United States Patent
Blum et al.

(10) Patent No.: US 8,715,923 B2
(45) Date of Patent: May 6, 2014

(54) PROTEIN SCAFFOLDS AND VIRAL PARTICLES FOR DETECTING ANALYTES

(75) Inventors: Amy S Blum, Washington, DC (US);
Banahalli R Ratna, Alexandria, VA (US); Kim Sapsford, Springfield, VA (US); Gary J Vora, Washington, DC (US); Carissa M Soto, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1139 days.

(21) Appl. No.: 11/574,676

(22) PCT Filed: Aug. 1, 2005

(86) PCT No.: PCT/US2005/026914
§ 371 (c)(1),
(2), (4) Date: Mar. 5, 2007

(87) PCT Pub. No.: WO2006/124044
PCT Pub. Date: Nov. 23, 2006

(65) Prior Publication Data
US 2008/0220408 A1    Sep. 11, 2008

Related U.S. Application Data

(60) Provisional application No. 60/592,118, filed on Jul. 30, 2004.

(51) Int. Cl.
*C12Q 1/70*    (2006.01)
*C12N 7/00*    (2006.01)

(52) U.S. Cl.
USPC .......................................... 435/5; 435/235.1

(58) Field of Classification Search
None
See application file for complete search history.

(56) References Cited

U.S. PATENT DOCUMENTS

| | | | |
|---|---|---|---|
| 5,596,132 A | 1/1997 | Zaitlin et al. | |
| 5,874,087 A | 2/1999 | Lomonossoff et al. | |
| 5,958,422 A | 9/1999 | Lomonossoff | |
| 6,110,466 A | 8/2000 | Lomonossoff et al. | |
| 6,500,611 B2 * | 12/2002 | Mattson | 435/5 |
| 6,649,813 B2 | 11/2003 | Zaitlin et al. | |
| 6,884,623 B1 | 4/2005 | Lomonossoff et al. | |

OTHER PUBLICATIONS

Sepp, et al. Giardiavirus-Resistant Giardia lamblia Lacks a Virus Receptor on the Cell Membrane Surface. Journal of Virology, Mar. 1994, vol. 68, No. 3. p. 1426-1431.*

(Continued)

*Primary Examiner* — Zachariah Lucas
*Assistant Examiner* — Stuart W Snyder
(74) *Attorney, Agent, or Firm* — US Naval Research Laboratory; Joseph T. Grunkemeyer

(57) ABSTRACT

The present invention relates to compositions and methods for detecting analytes using detectably labeled fluorescent protein scaffolds. In certain embodiments of the invention, the scaffolds are viral particles in which the capsid viral structure provides a scaffold to attach detectably labeled fluorescent dyes and capture moieties that can be utilized to determine the presence of a desired analyte in a sample using any suitable method. The protein scaffold can contain amino acids carrying reactive groups (e.g., amines and thiols) that are spatially distributed on it with large enough separation to enable the attachment of a greater number of fluorescent label molecules without quenching.

22 Claims, 8 Drawing Sheets

(56) References Cited

OTHER PUBLICATIONS

Orum, et al. Efficient method for constructing comprehensive murine Fab antibody libraries desplayed on phage. Nucleic Acids Res. 1993, 21(19):4491-4498.*

Hoogenboom, HR. Selecting and screening recombinant antibody librariesNature Biotechnology. 2005; 23(9):1105-1116.*

Wang, et al., Natural Supramolecular Building Blocks: Wild-Type Cowpea Mosaic Virus. Chem. Biol., Jul. 2002, 9:805-811.*

Wang, et al., Natural Supramolecular Building Blocks: Cysteine-Added Mutants of Cowpea Mosaic Virus. Chem. Biol., Jul. 2002, 9:813-819.*

Gruber, et al. Anomalous Fluorescence Enhancement of Cy3 and Cy3.5 versus Anomalous Fluorescence Loss of Cy5 and Cy7 upon Covalent Linking to IgG and Non-covalent Binding to Avidin. Bioconjugate Chem. 2000, 11, 696-704.*

Buening, et al. Real time single molecule imaging of adeno-associated virus uptake in living cells. Blood. 2001; 98(1): 744-745.*

Zauner, et al. Tryptophan-to-Dye Fluorescence Energy Transfer Applied to Oxygen Sensing by Using Type-3 Copper Proteins. Chem. Eur. J. 2007; 13: 7085-7090.*

Wang et al., "Icosahedral Virus Particles as Addressable Nanoscale Building Blocks" Angew. Chem. Int. Ed. 2002, 41, No. 3, 459-462.

* cited by examiner

FIG. 8

```
                          SEQUENCE LISTING

<160> NUMBER OF SEQ ID NOS: 3

<210> SEQ ID NO 1
<211> LENGTH: 5
<212> TYPE: PRT
<213> ORGANISM: Artificial
<220> FEATURE:
<223> OTHER INFORMATION: Placed between positions 98 and 99 of EF-CPMV
      protein subunit

<400> SEQUENCE: 1

Gly Gly Cys Gly Gly
1               5

<210> SEQ ID NO 2
<211> LENGTH: 374
<212> TYPE: PRT
<213> ORGANISM: Cowpea mosaic virus

<400> SEQUENCE: 2

Met Glu Gln Asn Leu Phe Ala Leu Ser Leu Asp Asp Thr Ser Ser Val
1               5                   10                  15

Arg Gly Ser Leu Leu Asp Thr Lys Phe Ala Gln Thr Arg Val Leu Leu
            20                  25                  30
```

```
Ser Lys Ala Met Ala Gly Gly Asp Val Leu Leu Asp Glu Tyr Leu Tyr
            35                  40                  45

Asp Val Val Asn Gly Gln Asp Phe Arg Ala Thr Val Ala Phe Leu Arg
50                  55                  60

Thr His Val Ile Thr Gly Lys Ile Lys Val Thr Ala Thr Thr Asn Ile
65                  70                  75                  80

Ser Asp Asn Ser Gly Cys Cys Leu Met Leu Ala Ile Asn Ser Gly Val
                85                  90                  95

Arg Gly Lys Tyr Ser Thr Asp Val Tyr Thr Ile Cys Ser Gln Asp Ser
            100                 105                 110

Met Thr Trp Asn Pro Gly Cys Lys Lys Asn Phe Ser Phe Thr Phe Asn
        115                 120                 125

Pro Asn Pro Cys Gly Asp Ser Trp Ser Ala Glu Met Ile Ser Arg Ser
130                 135                 140

Arg Val Arg Met Thr Val Ile Cys Val Ser Gly Trp Thr Leu Ser Pro
145                 150                 155                 160

Thr Thr Asp Val Ile Ala Lys Leu Asp Trp Ser Ile Val Asn Glu Lys
                165                 170                 175

Cys Glu Pro Thr Ile Tyr His Leu Ala Asp Cys Gln Asn Trp Leu Pro
            180                 185                 190

Leu Asn Arg Trp Met Gly Lys Leu Thr Phe Pro Gln Gly Val Thr Ser
        195                 200                 205

Glu Val Arg Arg Met Pro Leu Ser Ile Gly Gly Ala Gly Ala Thr
210                 215                 220

Gln Ala Phe Leu Ala Asn Met Pro Asn Ser Trp Ile Ser Met Trp Arg
225                 230                 235                 240

Tyr Phe Arg Gly Glu Leu His Phe Glu Val Thr Lys Met Ser Ser Pro
                245                 250                 255

Tyr Ile Lys Ala Thr Val Thr Phe Leu Ile Ala Phe Gly Asn Leu Ser
            260                 265                 270

Asp Ala Phe Gly Phe Tyr Glu Ser Phe Pro His Arg Ile Val Gln Phe
        275                 280                 285

Ala Glu Val Glu Glu Lys Cys Thr Leu Val Phe Ser Gln Gln Glu Phe
290                 295                 300

Val Thr Ala Trp Ser Thr Gln Val Asn Pro Arg Thr Thr Leu Glu Ala
305                 310                 315                 320

Asp Gly Cys Pro Tyr Leu Tyr Ala Ile Ile His Asp Ser Thr Thr Gly
                325                 330                 335

Thr Ile Ser Gly Asp Phe Asn Leu Gly Val Lys Leu Val Gly Ile Lys
        340                 345                 350

Asp Phe Cys Gly Ile Gly Ser Asn Pro Gly Ile Asp Gly Ser Arg Leu
        355                 360                 365

Leu Gly Ala Ile Ala Gln
        370

<210> SEQ ID NO 3
<211> LENGTH: 213
<212> TYPE: PRT
<213> ORGANISM: Cowpea mosaic virus

<400> SEQUENCE: 3

Gly Pro Val Cys Ala Glu Ala Ser Asp Val Tyr Ser Pro Cys Met Ile
1               5                   10                  15

Ala Ser Thr Pro Pro Ala Pro Phe Ser Asp Val Thr Ala Val Thr Phe
            20                  25                  30
```

-continued

```
Asp Leu Ile Asn Gly Lys Ile Thr Pro Val Gly Asp Asp Asn Trp Asn
         35                  40                  45
Thr His Ile Tyr Asn Pro Pro Ile Met Asn Val Leu Arg Thr Ala Ala
     50                  55                  60
Trp Lys Ser Gly Thr Ile His Val Gln Leu Asn Val Arg Gly Ala Gly
 65              70                  75                  80
Val Lys Arg Ala Asp Trp Asp Gly Gln Val Phe Val Tyr Leu Arg Gln
                 85                  90                  95
Ser Met Asn Pro Glu Ser Tyr Asp Ala Arg Thr Phe Val Ile Ser Gln
             100                 105                 110
Pro Gly Ser Ala Met Leu Asn Phe Ser Phe Asp Ile Ile Gly Pro Asn
             115                 120                 125
Ser Gly Phe Glu Phe Ala Glu Ser Pro Trp Ala Asn Gln Thr Thr Trp
     130                 135                 140
Tyr Leu Glu Cys Val Ala Thr Asn Pro Arg Gln Ile Gln Gln Phe Glu
145                 150                 155                 160
Val Asn Met Arg Phe Asp Pro Asn Phe Arg Val Ala Gly Asn Ile Leu
                 165                 170                 175
Met Pro Pro Phe Pro Leu Ser Thr Glu Thr Pro Pro Leu Leu Lys Phe
             180                 185                 190
Arg Phe Arg Asp Ile Glu Arg Ser Lys Arg Ser Val Met Val Gly His
         195                 200                 205
Thr Ala Thr Ala Ala
         210
```

PROTEIN SCAFFOLDS AND VIRAL PARTICLES FOR DETECTING ANALYTES

This application claims the benefit of U.S. Provisional Application No. 60/592,118 filed Jul. 30, 2004, which is hereby incorporated by reference in its entirety.

GOVERNMENT RIGHTS

Research relating to this application was federally sponsored by NRL grant #N00173-99-1-G000. The U.S. Government may have certain rights in this invention.

BRIEF DESCRIPTION OF THE DRAWINGS

FIG. 8: (A) CCD image of sandwich immunoassays using EF-CPMV complex as the tracer. (B) Plot of net intensity for blank and positive regions of the slide: Camp. jejuni (columns [5] and [6]; rows [5*] and [6*]), Bot. Toxoid A (columns [1] and [2]; rows [3*] and [4*]) and SEB (columns [3] and [4]; rows [1*] and [2*]). Note that the average standard deviation in the data is ~20%.

DESCRIPTION OF THE INVENTION

Figure 1:
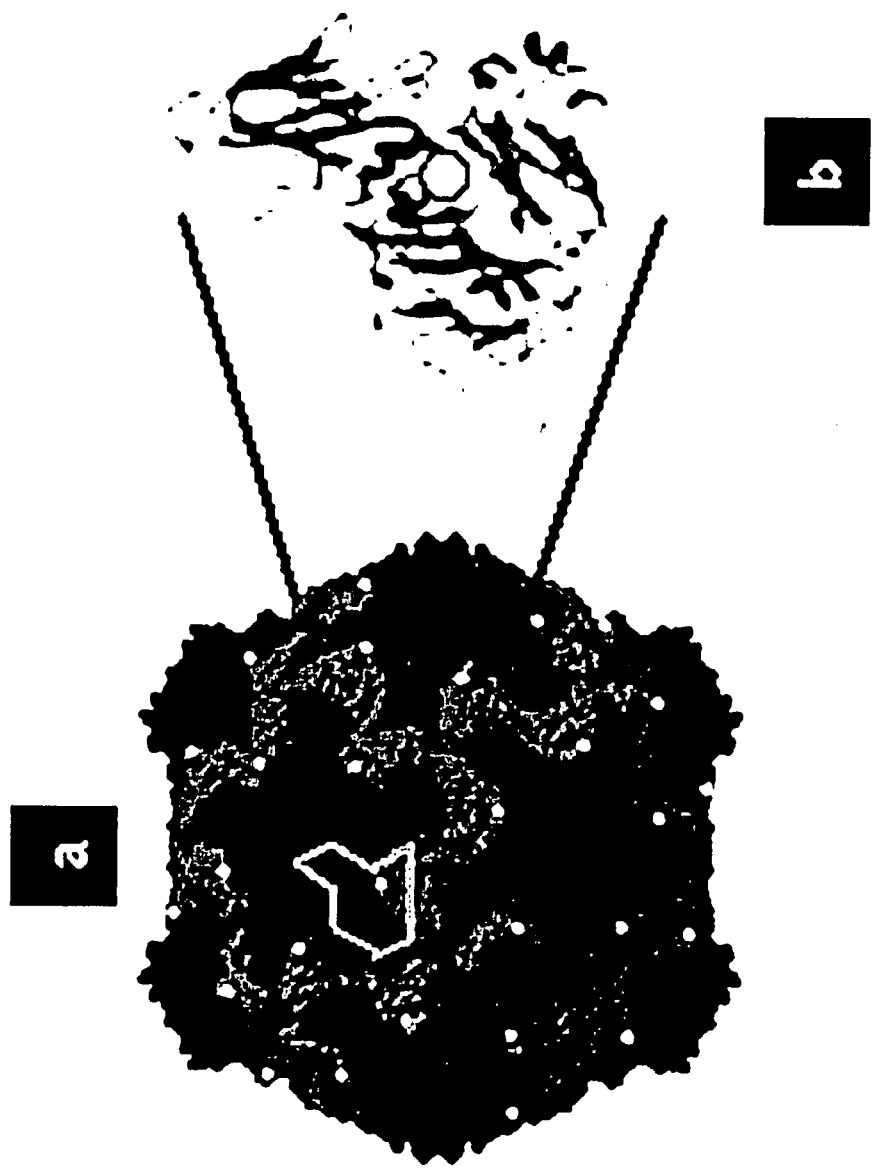
FIG. 1 Cysteine-mutant of Cowpea mosaic virus. a, A 30 nm diameter icosahedral virus particle, EF-CPMV, made of 60 identical protein subunits containing a total of 60 cysteines (thiol-containing group shown as white circles). b, EF-CPMV protein subunit to which a single cysteine was incorporated via the addition of a five residue loop (GGCGG) (SEQ ID NO: 1) placed between positions 98 and 99 (16).

The present invention relates to compositions and methods for detecting analytes using detectably labeled fluorescent protein scaffolds. In certain embodiments of the invention, the scaffolds are viral particles in which the capsid viral structure provides a scaffold to attach detection and/or capture moieties that can be utilized to determine the presence of a desired analyte in a sample using any suitable method.

The detection of analytes in samples is of major importance to a wide range of applications, including, medical, environmental science, forensic science, and food technologies. A key issue is how to increase the sensitivity of detection schemes to permit very small quantities of analyte to be detected. One strategy is to increase the amount of detectable label per reaction site to boost the signal intensity. When the detectable label is a fluorophore, however, there is a limitation on how many fluorophore molecules can be loaded on to a reaction site because adjacent fluorophores can self-quench. See, e.g., Schobel et al., Bioconjugate Chem., 10:1107-1114, 1999; Anderson and Nerurkar, J. Immunol. Methods, 271:17-24, 2002. Quenching can occur through the formation of dimers between neighboring fluorophore molecules.

The present invention provides a protein scaffold in which amino acids carrying reactive groups (e.g., amines and thiols) are spatially distributed on it with large enough separation to enable the attachment of a greater number of fluorescent label molecules without quenching. As a result, enhanced signals are generated with a corresponding increase in assay sensitivity. This approach is generally applicable to any technology that uses detectable label molecules which are susceptible to quenching.

In one aspect of the invention, compositions are provided for detecting analytes that include a protein scaffold which comprises: (a) at least one analyte binding moiety attached to the protein scaffold; and (b) a plurality of detectable fluorescent labels attached to the protein scaffold of the particle; wherein the detectable fluorescent labels are sufficiently distanced from each other to prevent or reduce fluorescence quenching between neighboring detectable fluorescent labels. The present invention also provides methods of making these protein scaffolds.

The protein scaffold can be comprised of any protein(s) that contains reactive groups for facilitating the attachment to it of analyte binding moieties and detectable fluorescent labels. The detectable labels are attached to the protein backbone in such positions ("sufficiently distanced") to reduce fluorescence quenching between neighboring detectable fluorescent labels. This can be achieved by spacing the labels at appropriate distances from each other to prevent quenching, such as the quenching associated with dimer formation. Any suitable spacing can be utilized as long as quenching is not substantially observed.

The distances are known for many fluorophores, but can also be determined experimentally, where increasing amount of label is incorporated into the protein scaffold, and the concomitant effect on fluorescence is measured. If no quenching effect is observed, then the amount of signal should increase (e.g., linearly). However, if the resulting signal does not increase, and even decreases in its intensity, this indicates that quenching may be occurring.

A protein scaffold can be selected which comprises amino acid residues containing reactive groups that are spaced at such distances that reduce the chance of dimer formation. This can be achieved by using naturally occurring polypeptides, which when folded, contain surface exposed reactive residues with the optimal spacing requirements. Genetic modification can also be used to genetically engineer a scaffold by the introduction of reactive groups (via amino acids) such that, when the protein is folded into its three-dimensional configuration, suitable spacing is achieved. Methods of genetically modifying protein sequences are well known in the art. For general methods of genetic engineering, see, e.g., Sambrook and Russell, *Molecular Cloning*, CSH Press, 3$^{rd}$ Edition, 2001; Howe, *Gene Cloning and Manipulation*, Cambridge University Press, 1995; Ausubel et al., *Current Protocols in Molecular Biology*, John Wiley & Sons, Inc., 2005.

The phrase "to prevent fluorescence quenching between neighboring detectable fluorescent labels" indicates that there is a substantial absence of quenching. Some quenching can occur, e.g., due to incorporation of label at unintended sites or misfolded portions of the protein scaffold, but this is a small fraction as compared to the absence of quenching along the complete scaffolding surface. The compositions can also be described as "reducing fluorescence quenching between neighboring detectable fluorescent labels," where the reduction is in comparison to a labeled scaffold where the spacing between fluorophores does not diminish quenching (e.g., separation is insufficient and quenching between neighboring fluorophores occurs).

Any suitable protein scaffold can be used in accordance with the present invention. In one aspect of the invention, scaffolds are utilized which themselves associate into a multimeric structures, increasing the number of available reactive sites for attaching capture and detection moieties. Any de novo designed polypeptide with reactive groups (e.g., cysteines or lysines) at controlled distances can be used. Another protein class that can be used includes chaperoning, including group I and group II chaperoning. See, e.g., worldwide web at cpndb.cbr.nrc.ca for a database of chaperoning. Hill et al., Genome Res. 14:1669-1675.

The examples below show the use of cowpea mosaic virus ("CPMV"), a non-enveloped viral particle. A non-enveloped viral particle is a virion that comprises assembled coat or capsid proteins, which is optionally associated with a viral genome or nucleic acid of interest. Viral particles can be produced routinely using any suitable method, including tissue culture, host cell lines, etc.

CPMV can be prepared routinely, e.g., using the methods described in Klootwijk et al., *Cell*, 11: 73, 1977. The capsid comprises two subunits, a small subunit (e.g., NP_734002) and a large subunit (e.g., NP_734001). RNA2 (e.g., NC_003550) codes for the two capsid proteins and the movement protein, which are involved in cell-to-cell transport of the virus. A sequence of the large protein is shown in SEQ ID NO: 2, and a sequence of the small subunit is shown in SEQ ID NO: 3, but see also the following references which describe the particular mutations and sequences utilized in the examples, Wang et al., Angew. Chem. Int. Ed., 2002, 41, 459; Wang et al., Chem. Biol., 2002, 9, 813; Blum et al., Nano Lett., 2004, 4, 867.

In addition to the naturally occurring CPMV virus, genetically engineered or mutant versions can be utilized. For instance, mutant versions can be used in which one or more amino acids of the naturally-occurring sequence are replaced by amino acids that comprise an R-group capable of being linked to an analyte-binding moiety or a detectable label. Useful amino acids include, lysine, cysteine, glutamic acid, aspartic acid, etc. When the viral particle is utilized as the scaffolding, the mutated or engineered subunits can be designed and selected such that they retain their ability to assemble into virions.

Although any non-enveloped virus can be used, Cow Pea Mosaic Virus exemplified because its structure is well studied and a number of stable mutants are available. In general, cysteines and lysines are the two most useful residues for functionalizing proteins in CPMV. Because the virus consists of 60 identical subunits, a single cysteine insertion presents 60 cys residues on the surface (e.g., between residues 98 and 99). These residues are arranged in specific patterns depending on the position of the inserted cys residue on the protein. Creating double-valent mutants where two cysteines are introduced in each subunit can also alter the distance between the neighboring cys residues and double the number of cysteine groups on the surface to 120. These virus mutants provide a scaffold to attach a large number of fluorophores with distances between neighboring dyes larger than their Forster distance, thus preventing the self quenching of the dyes. In addition to these fluorophores, a small number of proteins such as antibodies of interest or haptens (e.g., biotin for the gene arrays) can be attached either to the cysteines or to the lysines. Examples of useful CPMV mutations include EF-CPMV and DM-CPMV. See, e.g., Wang et al., Angew. Chem. Int. Ed., 2002, 41, 459; Wang et al., Chem. Biol., 2002, 9, 813; Blum et al., Nano Lett., 2004, 4, 867.

The lysine and cysteine residues can be independently modified and coupled to a fluorescent label or analyte-binding moiety. See, e.g., Wang et al., Chem. Biol., 2002, 9, 813, which describes methods for selectively modifying lysine or cysteine residues. In preferred embodiments, the present invention relates to CPMV particles in which cysteines are labeled with a fluorescent label, but substantially no lysines are labeled with it; or particles in which lysines are labeled with a fluorescent label, but substantially no cysteines are labeled with it. Where cysteines are labeled with the fluorescent label, lysines can be labeled with the analyte-binding moiety; and vice-versa. Preferred labeling positions include, lysine-38 of small subunit; insertions between residues 98 and 99 of the large subunit; insertions or substitutions at positions 28 and 102 of the large subunit, or 1 amino acid before or after such positions.

Particles can be comprised solely of wild-type or mutated capsid protein, or they can be comprised of a combination, as well as capsid proteins from other viruses (e.g., hybrid or chimeric viral particles).

As indicated, any non-enveloped virion can be utilized in accordance with the present invention. These include, but are not limited to, adenovirus, plant viruses such as tobacco mosaic virus (TMV), REO 3, PPV, SV40, HAV, including their representative generic classes.

A protein scaffold can be attached to analyte-binding moieties and detectable labels. An analyte-binding moiety can be any structure or compound that specifically attaches to a target analyte. It can also be referred to as a capture moiety. Examples of analyte-binding moieties, include, but are not limited to, antibodies (e.g., which are antigen-specific), oligonucleotides which are targeted to specific nucleotide sequences, aptamers, lectins, avidin, biotin, and any material which is useful for recognizing a targeted substance.

Any antibody type can be utilized as an analyte-binding moiety, including, e.g., monoclonal, polyclonal, single chain, IgG, Fab, and other fragments, etc. The analyte-binding moiety can be directly attached to an amino acid of the protein scaffold or it can be attached indirectly, e.g., using an avidin-biotin pair (see examples below) or other binding pairs. Spacers can also be used to create a desired distance between the scaffold surface and the binding moiety (or detectable label).

A detectable fluorescent label (or marker) can comprise any fluorescent material that enables its presence or absence to be determined. Examples of fluorescent dyes include, but are not limited to, Alexa Fluor 35, 488, 532, 546, 555, 568, 594, 647, 660, and 680; Fluorescein (FITC); SpectrumGreen; Rhodamine 6G; tetramethylrhodamine (TRITC); SpectrumOrange; Lissamine rhodamine B dye; Texas Red dye, SpectrumRed, PE; APC; Cy5; Cy5.5; Cy7; quantum dots; fluorescent microspheres (see e.g., U.S. Pat. No. 5,786,219), including spheres with magnetic properties (e.g., U.S. Pat. Application No. 20010046602); etc.

Attachment to the protein scaffold can be achieved by any suitable method, and includes both covalent and non-covalent attachment. In the examples, the side chain of lysine (amino) and cysteine (—SH) residues provides a reactive group for covalently attaching analyte binding moieties and labels, but the invention is not limited to these. In addition to amino acids, carbohydrates, lipids, and other moieties attached to the protein background can serve as a reactive group for coupling fluorescent dyer and capture moieties. Methods of modifying proteins are conventional and well-known in the art. For a complete discussion of coupling fluorescent dyes, see e.g., *Introduction to Fluorescence Techniques*, Invitrogen (available on the world wide web at probes.invitrogen.com/handbook/).

The amino group of lysine is a common target for chemical modification. Based on water solubility, amine-reactive reagents include NHS esters and sulfo-NHS esters. For reactions in aqueous solution, NHS esters are dissolved in an organic solvent, then diluted into the aqueous reaction mixture. The most commonly used organic solvents for this purpose are DMSO and DMF. These solvents are compatible with most proteins at 20% final concentration. Sulfo-NHS esters of biotin are soluble up to approximately 10 mM in water. Sulfo-NHS esters can be dissolved in water just before use, because these compounds are very prone to hydrolysis in solution. Even with the NHS esters, the solvents used to initially dissolve them are hygroscopic and promote hydrolysis of the NHS ester.

Cysteine on the surface of a protein or within a peptide comprises sulfhydryl groups (—SH or thiol groups) which is another target for chemical modification. Reactions are typically performed buffers free of extraneous sulfhydryls. Therefore, substances such as 2-mercaptoethanol, dithiothreitol, glutathione and mercaptoethylamine are usually removed before chemical modification proceeds. The common thiol-reactive functional groups are primarily alkylating reagents, including iodoacetamides, maleimides, benzylic halides and bromomethylketones.

Any material of interest (the "analyte") can be detected in accordance with the methods of the present invention. These include, nucleic acids (e.g., DNA, RNA, tRNA, mRNA, rRNA, etc), polypeptides (e.g., cell antigens, antibodies, etc), carbohydrates (e.g., attached as side chains to polypeptides), lipids (e.g., cholesterol), organic molecules, haptens etc. The term "hapten" is used broadly to include any material which can be specifically recognized by an analyte binding moiety, including epitopes, but also other materials which may or may not be able to induce an antigenic response, including, but are not limited to, biotin, avidin, neutravidin, etc.

The present invention also relates to methods of using the labeled protein scaffolds to detect analytes. The detection methods can be performed in any suitable manner or method. Analyte detection can be accomplished in a fluid phase, or solid phase, e.g., immobilized on a slide or within the walls of a fiber, or a DNA microarray format. For example, analytes can be present in cells or tissue sections, and detection can be performed using standard immunocytochemistry techniques, where the detectable label is prepared in accordance with the present invention. Microarrays of analytes can also be used, including arrays of proteins, nucleic acids, and antibodies, including arrays disclosed in U.S. Pat. Nos. 6,156,501; 6,077,673; 6,054,270; 5,723,320; 5,700,637; WO09919711; WO00023803. The probes are associated with the solid support in any effective way. For instance, the probes can be bound to the solid support, either by polymerizing the probes on the substrate, or by attaching a probe to the substrate. Association can be, covalent, electrostatic, noncovalent, hydrophobic, hydrophilic, noncovalent, coordination, adsorbed, absorbed, polar, etc. When fibers or hollow filaments are utilized for the array, the probes can fill the hollow orifice, be absorbed into the solid filament, be attached to the surface of the orifice, etc. Probes can be of any effective size, sequence identity, composition, etc., as already discussed. See, also: Rampal, J. B., Ed., DNA Arrays: Methods and Protocols (Methods in Molecular Biology, Volume 170), Humana Press (2001); Schena, M., Ed., DNA Microarrays: A Practical Approach, Oxford University Press (1999); Schena, M., Ed., Microarray Biochip Technology, BioTechniques Press (2000). Microarrays can be used to detect pathogens in the environment, for sequencing, for genotyping (e.g., SNPOs, haplotypes, etc.

The labeled protein scaffolds can be used in any method of analyte detection, especially methods which use oligonucleotides, antibodies, and other binding moieties. The compositions of the present invention can be substituted for any fluorescent label in a detection method. Methods include, but are not limited to, DNA hybridization assays, protein detection assays, microbial detection assays, immunoassays, fluorescent immunoassays (e.g., based on ELISA format), immunofluorescence, flow cytometry, histology, Western blot, PCR-based assays for detection of product, in situ nucleic acid hybridization (e.g., FISH), real-time fluorescence-based monitoring (e.g., U.S. Pat. No. 5,928,907).

As described in more detail in the examples, when polynucleotide detection is to be performed, the polynucleotide probes (e.g., bound to a surface) can incorporate a moiety that can be used to capture the labeled scaffold particle. For example, a polynucleotide can be prepared with biotinylated nucleotides (e.g., by PCR or nick-translation), where the biotin molecule is used to capture a protein scaffold that contains avidin or neutravidin. End-labeling can also be utilized.

Various strategies can be utilized to label polynucleotides with moieties that can be specifically recognized by a capture moiety on a protein scaffold of the present invention. These include, but are not limited to: hapten-labeled nucleotides that can be enzymatically incorporated into DNA or RNA probes; unlabeled aminoallyl derivatives of dUTP and UTP, as well as unlabeled and labeled aminohexylacrylamide (aha) derivatives of dUTP, that can be enzymatically incorporated into nucleic acids for subsequent conjugation with amine-reactive probes; ULYSIS Nucleic Acid Labeling Kits, which employ a chemical method for labeling nucleic acids without enzymatic incorporation of labeled nucleotides.

For example, an amine-modified nucleotide, 5-(3-aminoallyl)-dUTP can be incorporated into DNA using conventional enzymatic labeling methods. This step ensures relatively uniform labeling of the probe with primary amine groups. The aminoallyl dUTP substrate used in this reaction is taken up efficiently by reverse transcription or nick translation. In the second step, the amine-modified DNA is chemically labeled using an amine-reactive hapten.

ULYSIS is a patented Universal Linkage System (ULS) platinum-based chemistry (e.g., Van Gijlswijk R. P. M. et al., Universal Linkage System: versatile nucleic acid labeling technique, Expert Rev. Mol. Diagn., Vol. 1, p. 81-91, 2001). The system can be used to label both proteins and nucleic acids. ULS labels proteins by forming a coordinative bond on the sulphur atoms of methionine, cysteine and the nitrogen atom of histidine. ULS labels DNA, RNA and nucleotides by forming a coordinative bond on the N7 position of guanine. The ULS can be covalently bound to a fluorophore or hapten (depending on the purpose), such that when it attaches coordinately to its target, it also carries the desired capture or detectable label moiety.

Methods of detecting an analytes can comprise one or more of the following steps in any effective order, e.g., contacting said analyte with a non-enveloped viral particle comprising: (a) at least one analyte binding moiety attached to a capsid protein of the viral particle; and (b) a plurality of detectable fluorescent labels attached to capsid proteins of the particle, under conditions effective for the analyte binding moiety to bind to the analyte, wherein the detectable fluorescent labels are sufficiently distanced from each other to prevent fluorescence quenching between neighboring detectable fluorescent labels; and detecting binding between the analyte and the analyte binding region of the viral particle or detecting the fluorescence of said viral particle when bound to said analyte, wherein the presence of said analyte is identified. Detection can be desirable for a variety of different purposes, including for research, diagnostic, prognostic, and forensic purposes.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Contacting the sample with probe can be carried out by any effective means in any effective environment. It can be accomplished in a solid, liquid, frozen, gaseous, amorphous, solidified, coagulated, colloid, etc., mixtures thereof, matrix. For instance, a probe in an aqueous medium can be contacted with a sample which is also in an aqueous medium, or which is affixed to a solid matrix, or vice-versa.

Generally, as used throughout the specification, the term "effective conditions" means, e.g., the particular milieu in which the desired effect is achieved, including any agent or condition that is necessary to accomplish the desired purpose. Examples of conditions and/or agents, include, e.g., buffers; oxidizing agents; reducing agents; pH; ion, salt, and detergent concentrations; temperature; etc.

Detecting binding between the analyte and the analyte binding region of the viral particle can be accomplished by detecting the fluorescence of the protein scaffold when bound to the analyte. In typical binding assays, the analyte is contacted with the protein scaffold under conditions where the two can bind specifically to each other, and then unbound scaffold is removed. The specific removal step depends on the format of the assay. The remaining scaffold is bound to the analyte, and its presence is detected by measuring the emission of the fluorescent dye.

The detecting step can be qualitative or quantitative. For certain purposes, it may be sufficient to know whether the analyte is present or absent from the sample. In these cases, it may be sufficient to simply determine whether the detected signal is above background or not. However, other applications may require that the amount of analyte present in the sample be determined. Quantitative measurements can be achieved by performing an assay using known concentrations of analyte to create a standard curve.

Detecting the fluorescence can be done conventionally. For example, when slide arrays are used, a sensor as described in Feldstein et al., *J. Biomed. Microdevices,* 1: 139-153, 1999, can be used to detect fluorescence. Fluorescent scanners can also be used to collect data from arrays. See, e.g., worldwide web at rana.lbl.gov/EisenSoftware.htm for software for performing analysis of fluorescent images of microarrays. See, also cmgm.stanford.edu/pbrown/mguide/index.html for a guide to producing microarrays.

The present invention also provides methods of detecting a target polynucleotide comprising one or more of the following steps in any effective order, e.g., contacting a target polynucleotide in a test sample with a polynucleotide probe comprising a hapten under conditions effective to form a hybrid between said probe and target; contacting said hybrid with a detectably labeled protein scaffold; and detecting the fluorescence of said protein scaffold when bound to said polynucleotide, wherein the presence of said polynucleotide is identified and wherein the hapten is an analyte which is specifically recognized by the by the analyte biding moiety of the viral particle.

The step of contacting the target and probe polynucleotides can be carried under conditions which enable the polynucleotides to specifically hybridize with each other to form a double-stranded hybrid. The phrase "specifically hybridize" indicates that the hybridization between single-stranded polynucleotides is based on nucleotide sequence complementarity. The effective conditions are selected such that the probe hybridizes to a defined target nucleic acid. For instance, if the detection of a target polynucleotide representing a the p53 gene is desired, a probe can be selected which can hybridize to such target gene under high stringent conditions, without significant hybridization to other genes in the sample. Stringency conditions are well known in the art, and are described in the above-mentioned manuals on genetic engineering.

When the method is performed on a DNA microarray comprising an ordered array of polynucleotides, the polynucleotides attached to the solid phase surface are referred to as the "probe polynucleotides."

The "polynucleotide targets" for the purpose of DNA microarray analysis can be a mixture of nucleic acids, such as a population of RNA or DNA which is extracted from a sample (e.g., from a tumor, biopsy, environmental or forensic sample). In order to detect whether the probe binds to the target nucleic acid, the target can be labeled with a fluorescently-labeled viral particle. Any method of attaching the particle to the probe can be utilized without limitation.

For example, the probes can contain a hapten which serves as the recognition site for the analyte binding moiety of the viral particle. The probe sample can incorporate a hapten according to any of the methods already mentioned, as well as other methods. For example, transcription based amplification systems can be utilized which enable the production of nucleic acid from template RNA or DNA using a promoter primer (e.g., U.S. Pat. Nos. 5,545,522 and 5,716,785), and where the synthesis is performed in the presence of oligonucleotide substrates that comprise a hapten moiety (e.g., biotinylated nucleotides or nucleotides which comprise reactive groups for attaching suitable haptens). Random-priming can also be used.

Polynucleotides in the probe sample can also be generated which contain a polynucleotide barcode or label which is incorporated using a transcription based amplification system. The label (e.g., polyA or polyT) can serve as an analyte binding site for an analyte binding moiety which comprising its complement (e.g., polyT or polyA).

The present invention also provides compositions and methods for detecting proteins. The proteins can be present in any format, including on glass slides (e.g., tissue sections), microtiter wells, and membranes. In one embodiment, the proteins are distributed in a protein array or protein clip which has a spot of either proteins or their ligands arranged in a predefined pattern, arrayed manually or by robots on to a suitable substrate, such as a coated glass slides, microplates, or membranes. Substrate can further be coated with or contain materials tat proteins can be readily attached to, including nitrocellulose, hydrogel polymers, synthetic polymers, etc. The arrays can comprise any protein of interest, including antibodies, enzymes, or substrates or ligands that interact with proteins. Proteins can be arrayed using suitable technology, e.g., as described in U.S. Pat. No. 6,800,849 (also for DNA arrays). Protein chips are widely commercially available and any conventional assay for using them can be adapted in accordance with the present invention, where the protein scaffold is used as a labeling reagent.

The present invention also provides methods of detecting a target polypeptide comprising one or more of the following steps in any effective order, e.g., contacting a target polypeptide in a test sample with a polypeptide probe under conditions effective for said target to bind to said probe to form a target-probe complex; contacting said complex with a viral particle as described above, wherein said viral particle comprises an analyte binding moiety which specifically recognizes said target polypeptide, and detecting the fluorescence of said viral particle when bound to said complex, wherein the presence of said target is identified.

When the target of interest is present in the sample, it can bind to the probe to form a complex between the two proteins. For example, when the probe is an antibody, and the target is a protein which binds to the antibody, the complex can be referred to as an antibody-antigen complex. To detect binding, the polypeptide target can display a site which can be specifically recognized by the analyte-binding moiety of the protein scaffold. This site can be a hapten (such as avidin, biotin, or a protein tag); an epitope of the target polypeptide; or site created by the formation of the complex. The choice of the analyte binding moiety on the protein scaffold will depend on the site incorporated into the target protein. These assays can be carried out routinely, where the label is a protein scaffold rather than another conventional label.

Protein or nucleic acid deposition or synthesis can be carried out by automated methods that employ in situ fluid deposition synthesis devices such as pulse-jet fluid deposition devices in which thermal or piezo pulse jet devices analogous to inkjet printing devices are employed to deposit fluids of biopolymeric precursor molecules on to a substrate surface. For example, Roda et al., Biotechniques (2000) 28:492-496, describe a method in which a conventional inkjet printer is used for the microdeposition of proteins. The cartridge was filled with the protein deposition solution using a microsyringe and sealed. U.S. patents disclosing thermal and/or piezo pulse jet deposition of biopolymer containing fluids onto a substrate include: U.S. Pat. Nos. 4,877,745; 5,449,754; 5,474,796; 5,658,802; 5,700,637; 5,958,342; 6,015,880 and 6,419,883. Other in situ fluid deposition synthesis methods and devices such as those that employ other technology such as spotting a fluid with a pin or acoustical focusing may also be employed for in situ synthesis.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The entire disclosure of all applications, patents and publications, cited above and in the figures are hereby incorporated by reference in their entirety, including U.S. Provisional Application No. 60/592,118 filed Jul. 30, 2004.

EXAMPLES

Example 1

Figure 2:
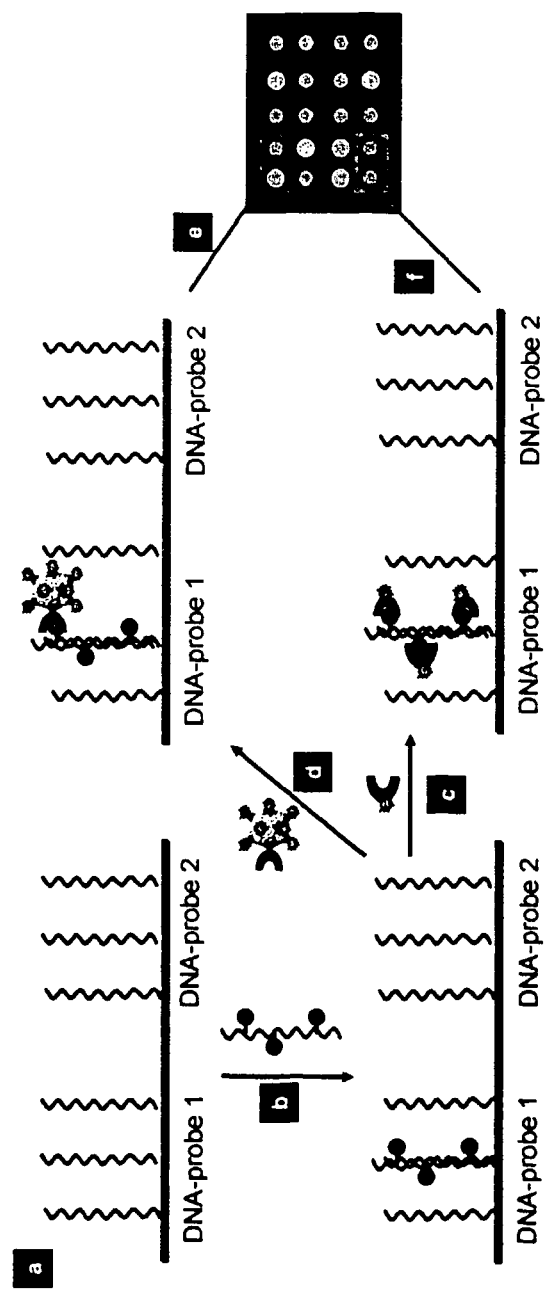
FIG. 2 DNA microarray detection scheme. a, DNA oligonucleotides 1 and 2 are immobilized in a microarray format on glass slides (probes). b, DNA probe-1 hybridizes with a previously amplified and biotinylated target DNA molecule. This hybridization event is detected using c, streptavidin-Cy5 or d, NA-Cy5-CPMV. e, Quantification post-detection indicates a true positive signal for the NA-Cy5-CPMV detection method (blue spot, hybridization with DNA-probe 1) or a true negative signal (gray spot, non-hybridization with DNA-probe 2). f, A false negative signal (gray spot) is observed for streptavidin-Cy5 as the total number of fluorophores at the DNA-probe 1 spot results in the generation of a signal that is below the detection threshold (or background).

Using standard maleimide coupling chemistry, we used the EF-CPMV as a scaffold for both Cy5 (>40 dyes per virus) and NeutrAvidin. Thus, the NeutrAvidin-Cy5-EF-CPMV nanoparticle (NA-Cy5-CPMV) acts as both a fluorescent signal generating element (via adducted Cy5 molecules) and as a recognition element for DNA molecules containing biotin (via adducted NeutrAvidin proteins). FIG. 2 shows the pathogen detection procedure schematically, demonstrating how NA-Cy5-CPMV can enhance sensitivity by dramatically increasing the number of dyes per biotin binding event, thus increasing the location concentration of dye vs. standard techniques, even though the amount of target DNA in solution remains the same.

Figure 3:
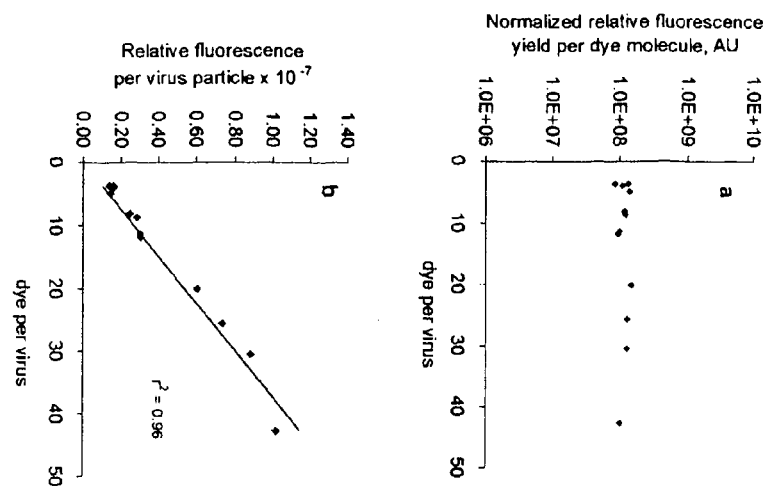
FIG. 3 Concentration dependence of fluorescence intensity in NA-Cy5-CPMV. a, Fluorescence yield at 666 nm was normalized against the dye concentration in solution using the dye absorbance at 605 nm. Constant intensity values up to 42 dyes/virus suggested a lack of quenching. b, Relative fluorescence per virus particle was defined as the ratio: fluorescence at 666 nm/absorbance at 260 nm. Solid line corresponds to the linear regression from the data shown as black diamonds.

A series of NA-Cy5-CPMV samples containing different dye per virus ratios in supplementary information) were prepared to determine the relative fluorescence yield as a function of dye per virus. The relative fluorescence normalized with respect to dye concentration (FIG. 3a) remained constant over a wide range of dye per virus ratios, suggesting lack of quenching in the virus conjugate even at high dye load of 42 dye/virus. This is further supported by the linear dependence of the fluorescence intensity on the number of dyes per virus as shown in FIG. 3b.

Figure 4:
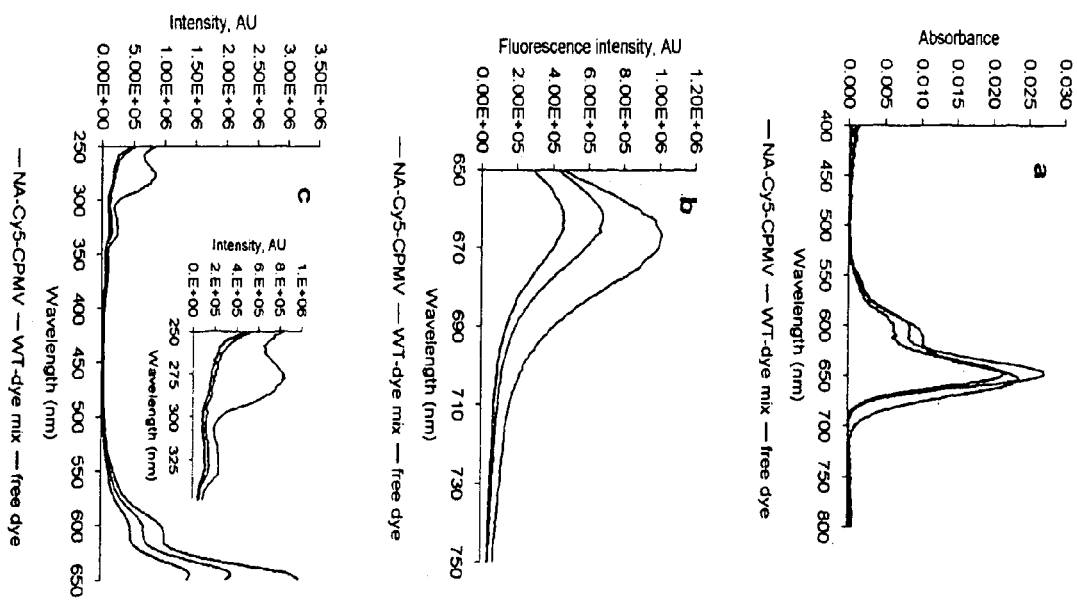
FIG. 4 Spectroscopic characterization of NA-Cy5-CPMV conjugates, WT-dye mix and free dye. a, UV-visible spectra showing absorbance of Cy5. b, Fluorescence spectra for the samples shown in a, excited at 605 nm. Fluorescence maximum is red-shifted for NA-Cy5-CPMV indicating that the dye is being coupled to the protein. c, Excitation scans of solutions shown in a and b, with the emission set at 665 nm. Peak at 280 nm on NA-Cy5-CPMV conjugate indicates energy transfer from the virus to the dye which is not present in the negative controls; WT-dye mix and free dye. Inset shows the scan from 250 nm to 350 nm.

The fluorescence yield of NA-Cy5-CPMV (EF-dye, 42 dye/virus; FIG. 4) was compared with two experimental controls: WT-dye mix (dye not bound to the viral protein scaffold) and free Cy5 in solution. The concentrations of both Cy5 (FIG. 4a) and virus were held comparable for all samples. The absorption spectrum for all the three samples were similar except for a small red shift in the main absorption peak for the EF-dye sample in which the Cy5 is covalently coupled to the virus. FIG. 4b shows fluorescence intensities under excitation at 605 nm for all three samples. Fluorescence intensities are on the same order of magnitude, but the presence of the virus particles slightly increases the fluorescence of unbound dye (WT-dye) and the covalent coupling of the dye to the virus increases the intensity even more. A red shift (2 nm) of the fluorescence maximum of EF-dye sample in comparison to the free dye is similar to that observed in absorption spectrum and is indicative of dye bound to protein(10).

Figure 5:
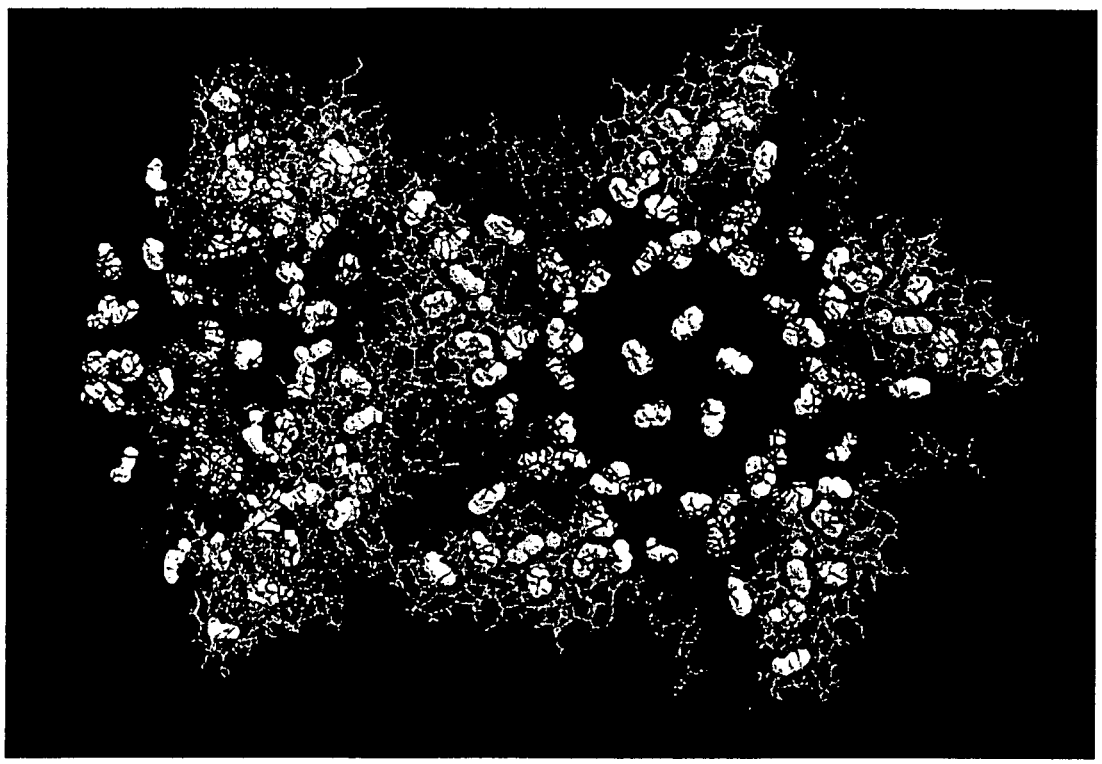
FIG. 5 Tryptophan residues distribution on EF-CPMV capsid. Crystallographic data from ten protein subunits of EF-CPMV generated using DeepView/Swiss-Pdb viewer version 3.7 software. Tryptophan groups are shown in white and EF-loop in yellow. Data used to calculate radial distribution of tryptophan groups with respect to the EF loop for distances from 10-60 Å (supplementary information).

In order to test the possibility of energy transfer between the protein and the dye in the NA-Cy5-CPMV samples excitation spectra were obtained (FIG. 4c) by keeping the emission wavelength at 665 nm, corresponding to emission from the Cy5 dye. All three samples show peaks at 605 nm and 650 nm, corresponding to the absorbance peaks for Cy5 (FIG. 4a). However, for the NA-Cy5-CPMV sample, an additional peak at 280 nm was present. This peak, which corresponds to the absorbance of the tryptophans in CPMV, is indicative of energy transfer from the virus to the dye. Since this peak was not present on the WT-dye control, we can conclude that the dye must be coupled to the protein surface in order for energy transfer to occur. Most of the natural fluorescence of CPMV comes from the tryptophan groups,(21) with average excitation maximum at 280 nm and emission maximum at 333 nm. Cy5 absorbs between 300-340 nm(22) which is in the spectral range of the virus emission. A total of 840 tryptophan groups are on the virus capsid, and all are within a radius of 100 Å to the EF loop (FIG. 5, Table 2S supplementary information) due to the symmetry of the capsid, allowing for efficient energy transfer from a large number of tryptophan groups to the EF-bound dye molecules.

Figure 6:
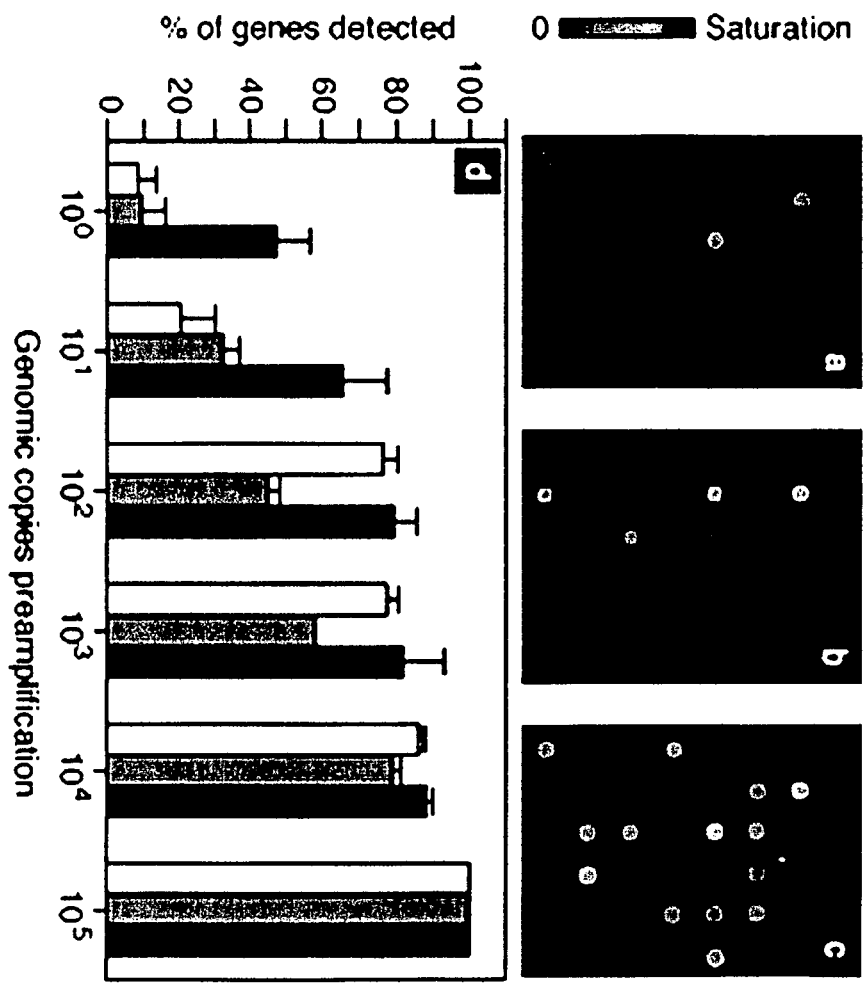
FIG. 6 Comparison of NA-Cy5-CPMV with commonly utilized microarray hybridization detection methods. Fluorescent microarray hybridization profiles of Vibrio cholerae 0139 amplified DNA ($10^1$ genomic copies starting material) detected via a, direct incorporation of Cy5-dCTP; b, Cy5-streptavidin; c, NA-Cy5-CPMV, 46 dye/virus. d, Graphical representation of the percentage of targeted genes detected as a function of preamplification genomic DNA copy number. Cy5-dCTP (white), Cy5-streptvidin (gray) and NA-Cy5-CPMV (black). The data shown represent means ±SD of three independent amplification and hybridization experiments.

Having demonstrated successful dye adduction in the absence of fluorophore quenching, we sought to test the utility of the NA-Cy5-CPMV nanoparticles in a comparative study for the detection and genotyping of *Vibrio cholerae* 0139 with the two most commonly used methods for microarray hybridization detection. Three detection methods were compared: i) direct enzymatic incorporation of Cy5-dCTP during DNA amplification (FIG. 6a), ii) direct enzymatic incorporation of biotin-14-dCTP during DNA amplification followed by detection with Cy5-labeled streptavidin (Cy5-streptavidin, FIG. 6b), and iii) direct enzymatic incorporation of biotin-14-dCTP during DNA amplification followed by detection with NA-Cy5-CPMV (FIG. 6c). As expected, when the amount of template DNA was not limiting (i.e. $10^5$ genomic copies, FIG. 6d) each of the three methods tested reliably detected 100% of the targeted genes. However, as the amount of template DNA was decreased via serial dilution, the viral nanoparticles outperformed the other two detection methods with respect to the percentage of targeted genes detected (FIG. 6d). This is clearly highlighted at the lowest template concentrations of $10^1$ and $10^0$ (FIG. 6a-d). Thus, in direct comparison with the two most often used methods of microarray hybridization detection, the NA-Cy5-CPMV nanoparticles provided the greatest overall detection sensitivity. It is important to note, that while a case could be made for polymerase-mediated label incorporation bias (Cy5-dCTP versus biotin-14-dCTP) when comparing the detection sensitivities of the Cy5-dCTP direct incorporation method with the NA-Cy5-CPMV, that case cannot be made when comparing Cy5-streptavidin and NA-Cy5-CPMV as the biotin-14-dCTP labelling method was used for both. Thus, the increase in detection sensitivity can be attributed solely to the fluorophore loading and the absence of fluorophore quenching. As a result, the nanoparticles have immediate utility for the detection of small samples or trace amounts of pathogen nucleic acids as the enhancement in detection sensitivity improves the lower limits of detection (genomic copy number or organisms) and reduces the risk of false negative determinations at low pathogen concentrations.

Based on this initial success, we proceeded to investigate the overall utility of the NA-Cy5-CPMV nanoparticles by comparing these nanoparticles with several other detection methods that have been used for microarray applications such as aminoallyl-dUTP, fluorophore conjugated antibodies, tyramide signal amplification, quantum dots and resonance light scattering (RLS) particles (see supplementary information). When criteria such as assay sensitivity, time, cost, ease of use and implementation into existing protocols are taken into consideration, we found that the NA-Cy5-CPMV nanoparticles compared favourably or consistently outperformed the other methods tested. Furthermore, the developed virus nanoparticles have one clear and practical advantage over technologies such as quantum dots and RLS particles—the engineered nanoparticles fit directly into existing detection platforms. As the vast majority of microarray scanners are outfitted with lasers that excite Cy3 and Cy5 organic dyes, we anticipate that the implementation of this reagent would enhance the sensitivity of existing assays without requiring any expenditure on the upgrade or purchase of new equipment.

Finally, although we have specifically addressed the use of the NA-Cy5-CPMV for microarray-based pathogen detection and genotyping assays, this tool may also have utility in any number of other microarray formats for the detection of single nucleotide polymorphisms, host expression profiling and simultaneous two colour or comparative expression profiling analyses. The enhancement of sensitivity afforded by the viral nanoparticles provides the opportunity to confidently detect small but significant changes in gene expression. The engineered EF-CPMV mutant can be readily manipulated. This fact combined with chemical crosslinking flexibility permits a plethora of molecular recognition, dye loading and multiplexing possibilities to develop assay sensitivity enhancing viral nanoparticles for microarray applications. Preliminary studies support this contention as NA-AlexaFluor 546-CPMV nanoparticles are compatible with and easily inserted into the existing high density Affymetrix GeneChip (23) platform and its accompanying protocols (data not shown). Current studies are underway to further enhance the fluorescent signal through the use of new mutants containing 120 cysteines per capsid, thus increasing the total dyes per virus.

Methods

Coupling of Maleimide-NeutrAvidin and Maleimide-Cy5 to EF-CPMV

One ml solution of 0.07 µM of virus sample (EF-CPMV) in 50 mM potassium phosphate buffer pH 7.0 mixed with 51 µl of 0.1 mM of maleimide-NeutrAvidin solution (prepared accordingly to manufacturer instructions, EZ-link maleimide activated NeutrAvidin Biotin-Binding Protein; Amersham Biosciences Corp., Piscataway, N.J., USA) was incubated overnight in the dark at room temperature (RT). Excess NeutrAvidin was removed by dialysis using 100 kDa MWCO (molecular weight cut off: Spectrapor; Fisher Scientific, Pittsburgh, Pa., USA) dialysis membrane against 50 mM potassium phosphate buffer pH 7.0 for 20 h exchanging the buffer every 4 h. Most of the recovered NeutrAvidin-virus solution (88%) was mixed with 16 µl of maleimide-Cy5 solution (10 µg/µl in DMSO; Sigma, St. Louis, Mo., USA) corresponding to an addition of 50 molar excess of the dye with respect to the total number of thiols on the virus capsid. Reaction was carried in 20% DMSO in a final volume of 1.5 ml. The reaction was incubated overnight at RT in the dark. Excess maleimide-Cy5 was removed by using size exclusion chromatography (HiTrap desalting columns; Amersham Biosciences Corp., Piscataway, N.J., USA). Two consecutive desalting columns were run using 50 mM K-phosphate buffer pH 7.0 as the eluent. Sample was eluted at the third column with PBS (137 mM NaCl, 2.7 mM KCl, 4.3 mM $Na_2HPO_4$, 1.4 mM $KH_2PO_4$, pH 7.3). For preparation of a series samples with different dye per virus ratio, variable amount of Cy5 was added to the reaction mix as described on the supplementary information.

Biotinylated Rhodamine Assay to Determine Presence of NeutrAvidin on NeutrAvidin-Containing Virus 12% of the reminder NeutrAvidin-virus solution was mixed with 2 µl of 1 mM biotinylated-rhodamine. The reaction was allowed to proceed for 4 h, followed by dialysis to remove unbound biotinylated-rhodamine. Dialysis against 50 mM K-phosphate buffer pH 7.0 was performed using a 50 kDa MWCO dialysis membrane, over a period of 24 h with buffer changes every 4 h.

Spectroscopic Characterization of NeutrAvidin-Cy5-Virus

UV-visible spectroscopy was performed to determine the amount of virus and dye present in the samples. Amount of virus was determined by using absorbance values of the peak at 260 nm (24). Amount of Cy5 dye was determined from its absorbance at 651 nm using the extinction coefficient provided by the manufacturer; baseline corrected using Peak Fit software, version 4.11 for samples having absorbance values <0.1. A Varian Cary 5000 UV-Vis Near IR spectrometer (software: Cary Win UV ScanApplication version 3.00) was used for UV-visible measurements.

Fluorescence intensity for rhodamine and Cy5 was determined by its emission at excitations wavelengths of 543 and 605 nm, respectively. Emission was set at 665 nm for excitation scans of Cy5-containing samples. Fluorescence measurements were carried in a Fluorolog (Jobin Yvon Horiba) fluorometer (software: data max for windows version 2.20) equipped with a temperature controller which was set at 20° C.

Multiplex PCR Amplification

*Vibrio cholerae* O139 genomic DNA was obtained from the American Type Culture Collection (51394D, Manassas, Va., USA) and used as the template for all amplification reactions. The gene targets, probes and primer sequences are listed in the supplementary information. Biotinylated 45-plex PCR reactions were performed in 50 □l volumes containing 1×PCR buffer (Qiagen Operon, Alameda, Calif., USA), 2.5 mM $MgCl_2$, 200 µM dATP, dGTP and dTTP, 20 µM dCTP, 20 µM biotin-14-dCTP (Invitrogen Life Technologies, Carlsbad, Calif., USA), 200 nM of each primer, 5 U Taq DNA polymerase (Qiagen) and $10^5$-$10^0$ copies of *V. cholerae* O139 genomic DNA. Cy5-dCTP-labeled amplicons were generated in a similar manner by replacing the 20 µM biotin-14-dCTP with 20 µM Cy5-dCTP (Amersham Biosciences Corp., Piscataway, N.J., USA). The amplification reactions were performed in a Peltier Thermal Cycler-PTC225 (MJ Research Inc., Reno, Nev., USA) with preliminary denaturation at 94° C. for 5 min. followed by 35 cycles of: 94° C. for 30 sec., 59° C. for 60 sec., 72° C. for 90 sec., and a final extension at 72° C. for 7 min. Upon completion, the amplified products were spin purified using the UltraClean PCR Clean-up Kit (Mo Bio Laboratories, Carlsbad, Calif., USA) and lyophilized.

Microarray Fabrication Hybridization and Detection

Seventy-mer oligonucleotide probes were designed and synthesized with a 5' amino modifier and 12 carbon spacer (Qiagen) and spotted onto 3-aminopropyltriethoxysilane (silanization)+1,4-phenylene diisothiocyanate (crosslinker)-modified glass slides for covalent probe immobilization as previously described (25). Once constructed, the spotted microarrays were blocked with a 3% bovine serum albumin-casein solution (BSA-C) for 15 min at room temperature and the slides were outfitted with MAUI Mixer DC hybridization chambers (BioMicro Systems, Salt Lake City, Utah, USA). Multiplex PCR lyophilized amplicon pellets were resuspended in 20 µl of hybridization buffer (4 µl 20×SSC, 4 µl formamide, 1 µl 3% BSA-C, 0.4 µl 10% SDS and 10.6 µl $dH_2O$), denatured for 3 min at 98° C. and immediately applied to the microarrays. Hybridizations were performed for 2 h at 63° C. on a MAUIHybridization System (BioMicro Systems). The slides were then washed twice with 4×SSC-0.2% SDS buffer for 3 min at 63° C. and twice with 2×SSC buffer for 1 min at room temperature. Slides that had received Cy5-dCTP-labeled amplicons were subsequently rinsed with $dH_2O$, dried and scanned. Slides that were hybridized with biotinylated amplicons were fitted with 22×25 LifterSlips (Erie Scientific Company, Portsmouth, N.H., USA) and prepared for probe-amplicon hybridization detection with either a Cy5-streptavidin (Amersham Biosciences) or the NA-Cy5-CPMV. The microarrays were incubated with 50 µl of 10 mM Cy5-streptavidin (0.5 µl Cy5-streptavidin, 2.5 µl 20×SSC, 47 µl BlockAid solution (Molecular Probes Inc., Eugene, Oreg., USA)) or 1×$10^{11}$ NA-Cy5-CPMV particles (10 µl CPMV, 2.5 µl 20×SSC, 37.5 µl BlockAid solution) for 30 min at room temperature. Fluorescent microarray images were captured with a ScanArray Lite confocal laser scanning system (PerkinElmer, Torrance, Calif., USA) at laser power 80 and Photo Multiplier Tube gain 80. Quantitative comparisons based on fluorescence intensities were made using the QuantArray analysis software package. The fluorescent signal from each microarray element was considered positive only when its quantified intensity was >2× that of known internal negative control elements. Three independent amplification and hybridization experiments were performed from each of the DNA template dilutions ($10^5$-$10^0$) for the hybridization detection methods interrogated.

References

1. Wang, D. et al. Viral discovery and sequence recovery using DNA microarrays. *PLoS Biol.* 1, e2 (2003).
2. Sevenet, N. & Cussenot, O. DNA microarrays in clinical practice: past, present, and future. *Clin Exp Med.* 3, 1-3 (2003).
3. Wang, D. et al. Microarray-based detection and genotyping of viral pathogens. *Proc Natl Acad Sci U S A.* 99, 15687-15692 (2002).
4. Duggan, D. J., Bittner, M., Chen, Y., Meltzer, P. & Trent, J. M. Expression profiling using cDNA microarrays. *Nat. Genet.* 21, 10-14 (1999).
5. Vora, G. J., Meador, C. E., Stenger, D. A. & Andreadis, J. A. Nucleic acid amplification strategies for DNA microarray-bases pathogen detection. *Applied and Environmental Microbiology* 70, 3047-3054 (2004).
6. Andras, S. C., Power, J. B., Cocking, E. C. & Davey, M. R. Strategies for signal amplification in nucleic acid detection. *Molecular Biotechnology* 19, 29-44 (2001).
7. Lisby, G. Application of nucleic acid amplification in clinical microbiology. *Molecular Biotechnology* 12, 75-99 (1999).
8. Lee, T. M. H., Li, L. L. & Hsing, I. M. Enhanced electrochemical detection of DNA hybridization based on electrode-surface modification. *Langmuir* 19, 4338-4343 (2003).
9. Greninger, D. A., Pathak, S., Talin, A. A. & Dentinger, P. M. Silver growth on micropatterned DNA chips: Effect of growth conditions and morphology on I—V behavior. *Journal of Nanoscience and Nanotechnology* 5, 409-415 (2005).

10. Schobel, U., Egelhaaf, H.-J., Brecht, A., Oelkrug, D. & Gauglitz, G. New donor-acceptor pair for fluorescent immunoassays by energy transfer. *Bioconjugate Chem.* 10, 1107-1114 (1999).

11. Anderson, G. P. & Nerurkar, N. L. Improved fluoroimmunoassays using the dye Alexa Fluor 647 with the RAPTOR, a fiber optic biosensor. *Journal of Immunological Methods* 271, 17-24 (2002).

12. Gruber, H. J. et al. Anomalous fluorescence enhancement of Cy3 and Cy3.5 versus anomalous fluorescence loss of Cy5 and Cy7 upon covalent linking to IgG and noncovalent binding to avidin. *Bioconjugate Chem.* 11, 696-704 (2000).

13. Johnson, J., Lin, T. & Lomonossoff, G. Presentation of heterologous peptides on plant viruses: Genetics, structure, and function. *Annu. Rev. Phytopathol.* 35, 67-86 (1997).

14. Lin, T. et al. The refine structure of cowpea mosaic virus at 2.8 A resolution. *Virology* 265, 20-34 (1999).

15. Wang, Q., Kaltgrad, E., Lin, T., Johnson, J. E. & Finn, M. G. Natural supramolecular building blocks: Wild-type cowpea mosaic virus. *Chemistry and Biology* 9, 805-811 (2002).

16. Wang, Q., Lin, T., Johnson, J. E. & Finn, M. G. Natural supramolecular building blocks: Cysteine-added mutants of cowpea mosaic virus. *Chemistry and Biology* 9, 813-819 (2002).

17. Wang, Q., Lin, T., L., T., Johnson, J. E. & Finn, M. G. Icosahedral virus particles as addressable nanoscale building blocks. *Angew. Chem. Int. Ed.* 41, 459-462 (2002).

18. Blum, A. S. et al. Cowpea mosaic virus as a scaffold for 3-D patterning of gold nanoparticles. *Nano Letters* 4, 867-870 (2004).

19. Soto, C. M. et al. Separation and recovery of intact gold-virus complex by agarose electrophoresis and electroelution: Application to the purification of cowpea mosaic virus and colloidal gold complex. *Electrophoresis* 25, 2901-2906 (2004).

20. Lakowicz, J. R. in *Principles of fluorescence spectroscopy* 257-301 (Plenum Press, New York, 1983).

21. Da Poian, A. T., Oliveira, A. C. & Silva, J. L. Cold denaturation of an icosahedral virus. The role of entropy in virus assembly. *Biochemistry* 34, 2672-2677 (1995).

22. Heilemann, M., Margeat, E., Kasper, R., Sauer, M. & Tinnefeld, P. Carbocyanine dyes as efficient reversible single-molecule optical switch. *J. Am. Chem. Soc.* 127, 3801-3806 (2005).

23. McGall, G. H. & Christians, F. C. High-density genechip oligonucleotide probe arrays. *Adv Biochem Eng Biotechnol.* 77, 21-42 (2002).

24. Chatterji, A. et al. New addresses on an addressable virus nanoblock: Uniquely reactive Lys residues on cowpea mosaic virus. *Chem. Biol.* 11, 855-863 (2004).

25. Charles P T et al. Fabrication and surface characterization of DNA microarrays using amine- and thiol-terminated oligonucleotide probes. *Langmuir* 19, 1586-1591 (2003).

Example 2

2.1. Functionalization of EF-CPMV with Dye, IgG and Antibodies

Figure 7:
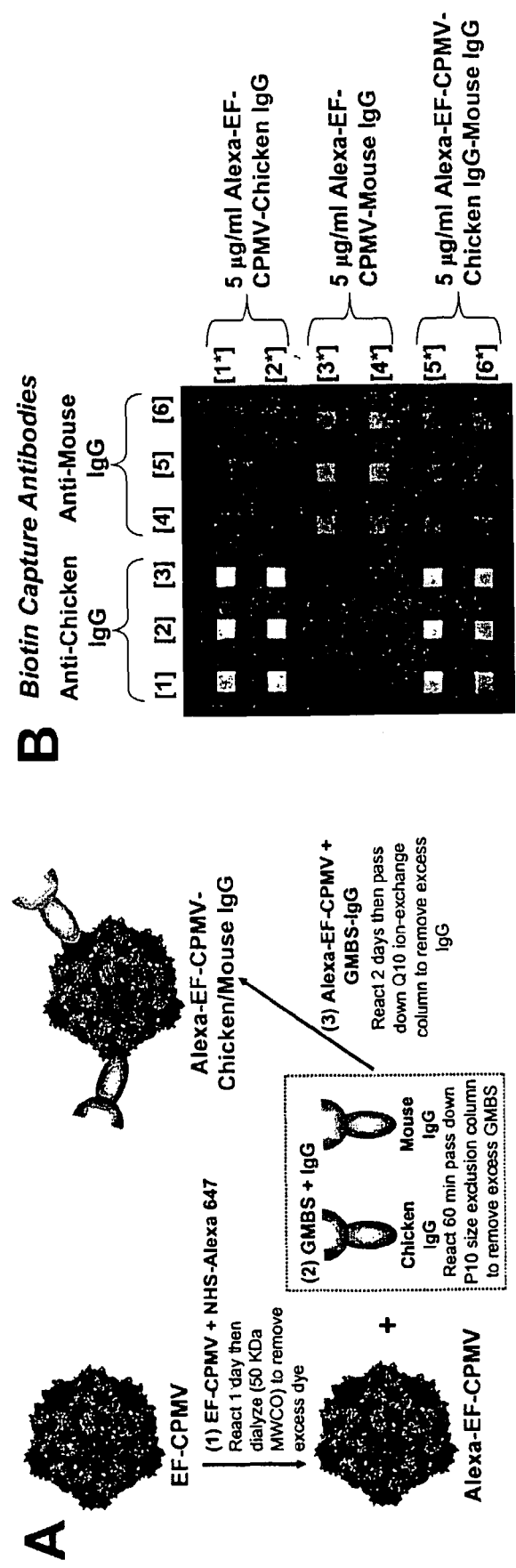
FIG. 7 (A) Schematic showing the procedure for modifying EF-CPMV with Alexa fluorescent dye and chicken and mouse IgG. (B) CCD image of the direct immunoassay taken using the NRL array biosensor.

The EF-CPMV was first labeled via the lysines with the succinimide ester functional dye, AlexaFluor 647 (Molecular Probes Inc.; Eugene, Oreg.), as outlined in FIG. 7A. EF-CPMV was prepared in borate buffer (50 mM), pH 9.0, and exposed to NHS-Ester-Alexa fluorescent dye at a ratio of ~3600 fluorophores to 1 viral particle. This mixture reacted for 2-3 hours at room temperature and then overnight at 4° C. The sample was dialyzed, using 50 KDa MWCO Spectra/Pore dialysis bags (Spectrum Laboratories Inc.; Rancho Domiguez, Calif.) against 50 mM phosphate buffer (PB) pH 7.4 (Sigma-Alrich; St. Louis, Mo.) to remove unreacted dye molecules.

Following purification by dialysis, the Alexa-EF-CPMV was exposed to either IgG proteins (chicken IgG and/or mouse IgG; Jackson ImmunoResearch; West Grove, Pa.) or antibodies to *Staphylococcus aureus* enterotoxin B (SEB) [polyclonal rabbit anti-SEB and SEB toxin from Toxin Technology Inc.; Sarasota, Fla.], botulinum toxin [polyclonal rabbit anti-Bot. toxin and botulinum toxoid A supplied by the U.S. Department of Defense Critical Reagents Program] or *Campylobacter jejuni* [polyclonal rabbit anti-*Camp. jejuni* supplied by Biodesign International; Saca, Me. and the bacteria *Camp. jejuni* (ATCC35918) grown by Dr. Avraham Rasooly (NIH) and used under Biosafety II conditions which required the cells to be killed with azide prior to shipment to the NRL], that had first been activated with the bifunctional linker N-(γ-maleimidobutyryloxy)succinimide ester (GMBS) (Fluka; Buchs SG, Switzerland). The IgG proteins and antibodies were prepared in 50 mM PB plus 0.15 M NaCl pH 7.2 (PBS) at a concentration of 1 mg/ml. GMBS, 1 mg/ml in dimethyl sulfoxide (DMSO) (Sigma-Aldrich, St. Louis, Mo.), was then added (90 µL) to each of the IgG/antibody solutions (1 mL). The solutions were allowed to react for 1 hour at room temperature (the succinimide ester of the GMBS reacts with the lysine groups on the IgG) and passed down a BioGel P-10 column (Bio-Rad; Hercules, Calif.) to remove unreacted GMBS. Following this purification step, the GMBS-functionalized IgG/antibodies were mixed with the Alexa-EF-CPMV sample, at a ratio of ~100 IgG to 1 virus and left to react at 4° C. for 2-3 days to allow the maleimide groups attached to the GMBS-species to react with the thiols present on the surface of the virus. The unreacted IgG/antibody was then removed from the IgG functionalized Alexa-EF-CPMV using a Q-10 Sepharose ion-exchange column (Amersham Biosciences Corp.; Piscataway, N.J.) and a NaCl gradient (100 mM Phosphate buffer+0.05% Tween+0-1.0 M NaCl). The virus was found to elute at a NaCl concentration of 0.5 M, while the free IgG or antibody eluted at 0.2 M NaCl. The collected fractions were concentrated using a 100 KDa MWCO Amicon Centriplus centrifugal filter (Millipore Corp.; Bedford, Mass.) and characterized using UV-visible and fluorescence spectroscopy.

2.2. Direct and Sandwich Immunoassays with Functionalized EF-CPMV

Figure 8:
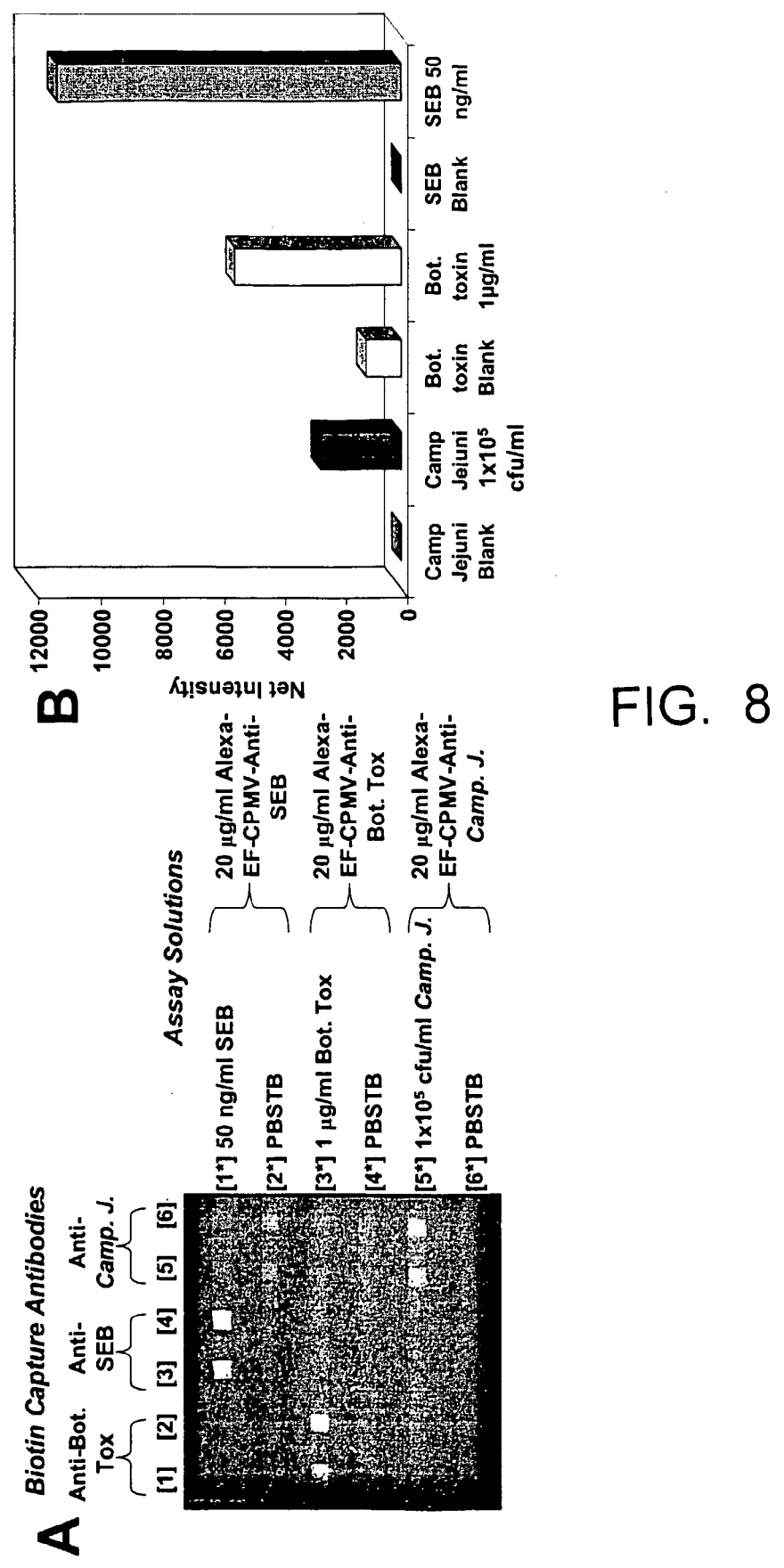

Glass microscope slides were prepared as described previously with covalently attached NeutrAvidin and were assembled with patterning poly(dimethylsiloxane) (PDMS) (Nusil Silicone Technology; Carpintera, Calif.) flow cells (Sapsford et al., 2004; Feldstein et al., 1999). For the direct immunoassays the channels were exposed to either biotinylated rabbit anti-chicken IgG or biotinylated goat anti-mouse IgG (Jackson ImmunoResearch; West Grove, Pa.), 10 µg/ml in PBS+0.05% Tween-20 (PBST), overnight in the fridge, 4° C. (columns [1]-[6]; FIG. 7B). The antibody functionalized slides were then assembled in assay PDMS flow cells, whose channels run perpendicular to the columns of patterned antibodies (rows [1*]-[6*]; FIG. 7B), and exposed for 1 hour at RT to 5 µg/ml Alexa-EF-CPMV functionalized with either chicken IgG, mouse IgG or both, prepared in PBST+0.1% BSA (PBSTB). The channels were then rinsed with 1 ml of PBSTB, the PDMS flow cell removed, the slide dried and imaged with the NRL array biosensor. The biosensor, equipped with a diode laser (633 nm) and a charge coupled device (CCD) camera, has been described previously (Feldstein et al., 1999). In the case of sandwich immunoassays NeutrAvidin slides were assembled with the patterning PDMS flow cells were exposed to either biotinylated rabbit anti-SEB, biotinylated rabbit anti-Bot. toxin or biotinylated rabbit anti-*Camp. jejuni*, 10 µg/ml in PBST, overnight in the fridge, 4° C. (columns [1]-[6]; FIG. 8A). The assay PDMS flow cells then attached, and the slides were exposed to either PBSTB or the target analytes; 50 ng/ml SEB, 1 µg/ml Bot. toxoid A or $1 \times 10^5$ cfu/ml *Camp. jejuni* for 30 min at RT (rows [1*]-[6*]; FIG. 8A). The channels were then rinsed and exposed for 1 h at RT to 20 µg/ml of the Alexa-EF-CPMV functionalized with the appropriate antibody (rows [1*]-[6*]; FIG. 8A), prepared in PBSTB. Following a final rinse with 1 ml of PBSTB, the PDMS flow cell was removed, the slide dried and imaged with the NRL array biosensor.

2.3. Functionalization of DM-CPMV with Dye and SEB Antibodies

In this modified scheme 1 mg/ml sheep-anti-SEB (250 µl) functionalized with GMBS was mixed with 200 µg of DM-CPMV in a final volume of 2 ml and incubated for 36 h. The sample was then concentrated to a final volume of 500 µl using a 100 k MWCO centrifugal filter (Microsep unit, MWCO=100 kDa; from VWR International; West Chester, Pa.). Excess anti-SEB was removed by size exclusion chromatography using a Superose 6 column (Amersham Biosciences: 18 cm long, 1 cm diameter, flow rate 0.5 ml/min) equilibrated with 100 mM PB pH 7.0. DM-CPMV containing fractions (determined by UV-visible spectroscopy; λmax=260 nm) were pooled and concentrated to a final volume of 400 µl using a 100 kDa centrifugal filter. The DM-CPMV-anti-SEB sample was incubated on ice for 5 min prior to the addition of 100 µl of DMSO followed by addition of 50 µl of 10 µg/µl of AlexaFluor 647-$C_2$-maleimide in DMSO (Molecular Probes Inc.; Eugene, Oreg.). The mixture was incubated at room temperature in the dark for 24 h at RT and 16 h at 4° C. The Alexa-DM-CPMV-anti-SEB sample was then purified using the Superose 6 column (size exclusion) and eluted with 50 mM (PB) pH 7.0 buffer, twice, to ensure complete removal of unreacted dye.

Figure 9:
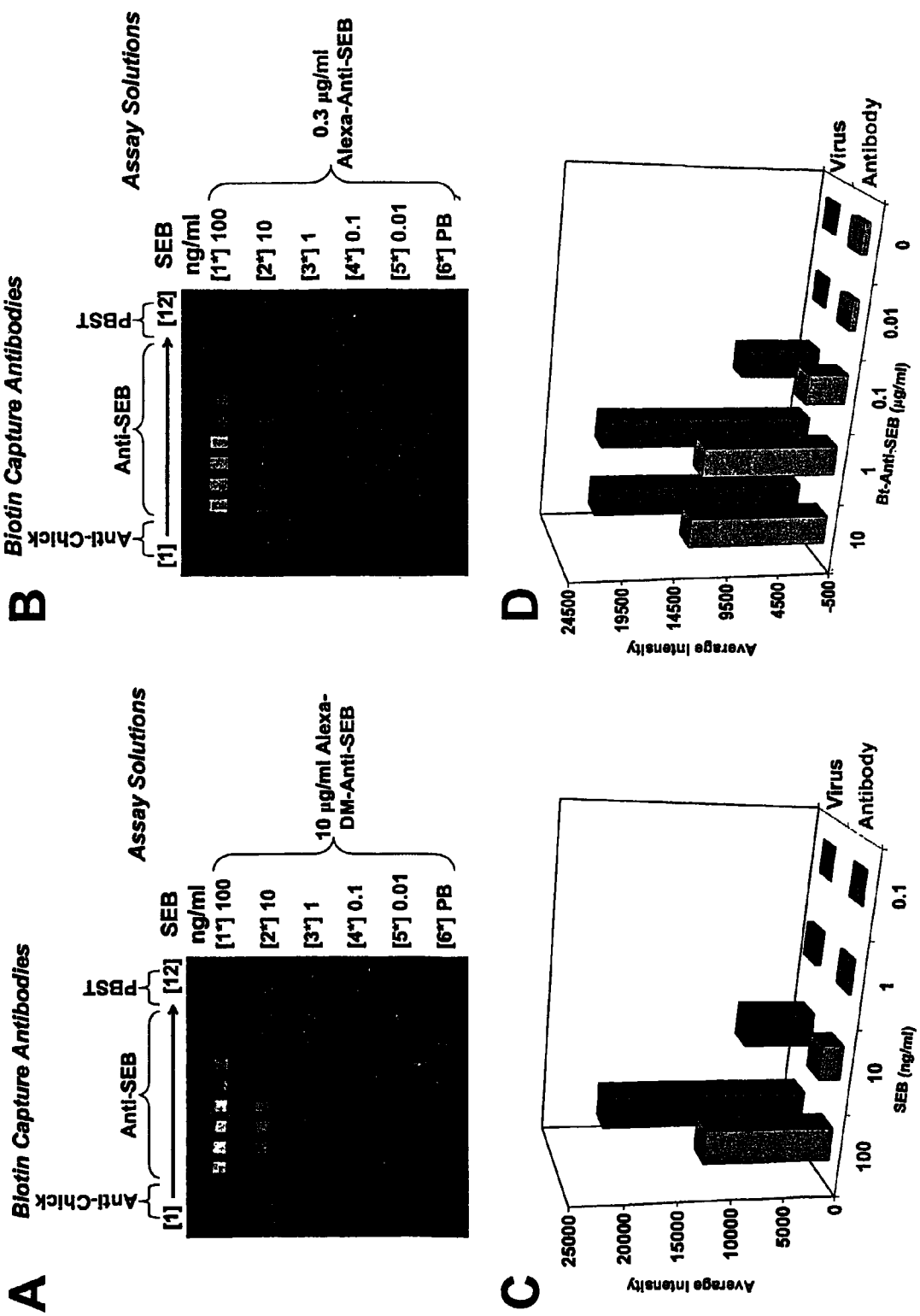
FIG. 9: (A) CCD image of SEB sandwich immunoassays using the Alexa-DM-CPMV-anti-SEB complex as the tracer. (B) CCD image of SEB sandwich immunoassays using Alexa-anti-SEB as the tracer. (C) Plot of net intensity versus SEB concentration exposed to the slide for the virus complex and antibody as tracer; at a biotinylated rabbit anti-SEB of 1 μg/ml. (D) Plot of net intensity versus concentration of the capture antibody exposed to the surface for the virus complex and antibody as tracer; at a SEB concentration of 100 ng/ml. Note that the average standard deviation in the data is ~10%.

NeutrAvidin slides were assembled with the patterning PDMS flow cells (12-channel) and the channels exposed to biotinylated rabbit anti-chicken 10 µg/ml in PBST, biotinylated rabbit anti-SEB 10-0.01 µg/ml in PBST, or PBST overnight in the fridge, 4° C. (columns [1]-[1,2]; FIGS. 9A and B). The assay PDMS flow cells then attached, and the slides were exposed varying concentrations of SEB (100-0.01 ng/ml) for 20 min at RT (rows [1*]-[6*]). The channels were then rinsed and exposed for 1 h at RT to either 10 µg/ml of the Alexa-DM-CPMV-anti-SEB (rows [1*]-[6*]; FIG. 9A) or 0.3 µg/ml Alexa-anti-SEB (rows [1*]-[6*]; FIG. 9B), prepared in 100 mM phosphate buffer (PB). The channels were rinsed with 1 ml of PB, the PDMS flow cell removed, the slide dried and imaged with the NRL array biosensor.

3. Results and Discussion

Initial experiments involved functionalizing EF-CPMV with dye and IgG protein. A total of three modifications of the Alexa-EF-CPMV were prepared: one modified with chicken IgG, one with mouse IgG and the final with both chicken and mouse IgG, as outlined in FIG. 7. This scheme takes advantage of the native lysines and inserted cysteines present on the CPMV to controllably functionalize its surface. The EF-CPMV was characterized after modification with Alexa dye and both chicken and mouse IgG by UV-visible spectroscopy giving the final ratio of Alexa 647:EF-CPMV as 13.7:1. Functionalization of the virus with dye and IgG was confirmed using a direct immunoassay using a rabbit anti-chicken IgG/goat anti-mouse IgG modified waveguide. FIG. 1B clearly demonstrates that the Alexa-EF-CPMV-chicken IgG was only captured by the rabbit-anti-chicken IgG and likewise the Alexa-EF-CPMV-mouse IgG by goat anti-mouse IgG as demonstrated by the increased signal intensity observed in these regions from the dual dye and IgG labeled virus. The lower intensity of the mouse regions as opposed to the chicken regions of the slide is due to the lower affinity of the goat anti-mouse IgG for mouse IgG relative to the rabbit anti-chicken IgG for chicken IgG, and has also been demonstrated in direct assays run with the Alexa-labeled IgGs (data not shown). The Alexa-EF-CPMV modified with both the chicken and mouse IgG, as expected, was captured by both the rabbit anti-chicken IgG and the goat anti-mouse IgG (FIG. 7B) with little effect on the final intensity reached relative to Alexa-EF-CPMV modified with a single protein species. This demonstrates that the dye-labeled virus, functionalized with up to two different species of IgG can be used as a tracer.

The next step was to immobilize functional antibodies to the surface of a dye-labeled virus and use the resulting complex as a tracer in sandwich immunoassays. For these studies Alexa-EF-CPMV was functionalized with antibodies to either *Staphylococcus aureus* enterotoxin B (SEB), botulinum toxin or *Campylobacter jejuni*. Experiments carried out using antibody pre-labeled with Cy3 (Amersham Biosciences Corp.; Piscataway, N.J.) fluorescent dye suggest that typically 3-5 proteins are attached to the virus surface using this conjugation procedure. The final CCD image is shown in FIG. 8A; clearly, the Alexa-EF-CPMV-antibody complex is only captured in the regions of the slide functionalized first with the appropriate capture antibody and second exposed to the correct analyte. For example, signal intensity is only observed for the Alexa-EF-CPMV-Anti-Bot. toxin in the columns [1] and [2] exposed to biotinylated rabbit anti-Bot. toxin and then only in row [3*] where the slide was first exposed to 1 µg/ml Bot. toxoid A and not in row [4*] where the analyte is not present. This is also true for the other sandwich immunoassays, SEB and *Camp. jejuni*, carried out. The images were analyzed using a custom software application written in LabWindows/CVI (National Instruments); the program creates a mask consisting of data squares (where the capture antibody is patterned) and background rectangles located on either side of a data square. The net intensities obtained by subtracting the average background signal from the average data signal for each Alexa-EF-CPMV-antibody complex are shown in FIG. 8B. The Alexa-EF-CPMV-anti-SEB was found to bind non-specifically to the biotinylated rabbit anti-Camp. jejuni columns ([5] and [6]) as observed by the low intensity observed in columns [5] and [6]; rows [1*] and [2*], FIG. 8A, but not to the biotinylated rabbit anti-Bot. toxin columns ([1] and [2]). This non-specific binding occurs in the presence and absence of SEB suggesting it is the Alexa-EF-CPMV-anti-SEB complex that is non-specifically binding and not the SEB. The non-specific binding of rabbit anti-SEB has previously been observed for Alexa-labeled rabbit anti-SEB (data not shown), suggesting it is an antibody issue and not an effect of the CPMV. These studies clearly demonstrate that once immobilized to the surface of the virus, the antibodies remain functional and bind to their specific analyte. In direct mole-to-mole comparisons between using standard Alexa-labeled antibodies and the Alexa-EF-CPMV-antibody complexes as tracers in immunoassays, however, we found that the plain antibodies gave a lower limit of detection (LOD). This is most likely an effect the fairly low dye-tovirus ratio obtained (Alexa 647:EF-CPMV) of 13.7:1 relative to the 4.5:1 for the dye-to-plain antibody.

One way to improve the LOD obtained by the Alexa-EF-CPMV-antibody complex was to increase the overall dye-to-virus ratio. In order to achieve this we developed an alternative scheme, which used a double CPMV mutant (DM-CPMV: 28/102 of the large subunit), containing 120 surface thiols, to increase the number of dyes-per-virus. In this scheme the DM-CPMV is first modified with the GMBS functionalized antibody, in this case sheep-anti-SEB, and then the Alexa-dye. However, unlike the initial scheme (FIG. 7A) both the antibody and the Alexa dye target the surface thiol groups. The final ratio of Alexa 647:DM-CPMV, characterized by UV-visible spectroscopy, was calculated to be 60:1, a factor of 4.4 improvement over the initial scheme.

Sandwich immunoassays were run to confirm successful modification of the DM-CPMV with both dye and anti-SEB antibodies and also to investigate potential improvements in the LOD. The final CCD images, FIGS. 9A and 9B, compare mole equivalent amounts of the Alexa-DM-CPMV-anti-SEB complex to the Alexa-anti-SEB when used as tracers in sandwich immunoassays for SEB, respectively. As seen from FIG. 9A the Alexa-DM-CPMV-anti-SEB complex only binds to the surface of the waveguide in the regions functionalized with both the capture anti-SEB antibody and the SEB analyte. The signal intensity is found to decrease as the concentration of the SEB in solution decreases. The same holds true when Alexa-anti-SEB is used as a tracer, FIG. 9B. The images were analyzed and the signal intensity plotted either as a function of the SEB concentration (FIG. 9C) or the concentration of the biotinylated rabbit anti-SEB (FIG. 9D). Clearly in both cases the Alexa-DM-CPMV-anti-SEB complex produces a stronger signal than the mole equivalent of Alexa-anti-SEB when used as a tracer demonstrating the advantage of CPMV as a nanoscaffold to couple active biomolecules and a larger number of reporter dye molecules on the same capsid.

References

Blum, A. S., Soto, C. M., Wilson, C. D., Cole, J. D., Kim, M., Gnade, B., Chatterji, A., Ochoa, W. F., Johnson, J. E., Ratna, B. R., 2004. Nano Lett. 4, 867-870.

Chatterji, A., Ochoa, W., Shamieh, L., Salakian, S. P., Wong, S. M., Clinton, G., Ghosh, P., Lin, T., Johnson, J. E., 2004a. Bioconjugate Chem. 15, 807-813.

Chatterji, A., Ochoa, W. F., Paine, M., Ratna, B. R., Johnson, J. E., Lin, T., 2004b. Chem. Biol. 11, 855-863.

Choi, J. W., Nam, Y. S., Fujihira, M., 2004. Nanoscale fabrication of biomolecular layer and its application to biodevices. Biotechnol. Bioprocess Eng. 9, 76-85.

Clark, J., Singer, E. M., Korns, D. R., Smith, S. S., 2004. BioTechniques 36, 992-1001.

Feldstein, M. J., Golden, J. P., Rowe, C. A., MacCraith, B. D., Ligler, F. S., 1999.

J. Biomed. Microdevices 1, 139-153.

Lin, T., Chen, Z., Usha, R., Stauffacher, C. V., Dai, J.-B., Schmidt, T., Johnson, J. E., 1999. Virology 265, 20-34.

Lomonossoff, G. P., Johnson, J. E., 1996. Curr. Opin. Struct. Biol. 6, 176-182.

Oakley, B. A., Hanna, D. M., 2004. IEEE Trans. Nanobiosci. 3, 74-84.

Park, S.-J., Lazarides, A. A., Storhoff, J. J., Pesce, L., Mirkin, C. A., 2004. J. Phys. Chem. B 108, 12375-12380.

Portney, N. G., Singh, K., Chaudhary, S., Destito, G., Schneemann, A., Manchester, M., Ozkan, M., 2005. Langmuir 21, 2098-2103.

Sapsford, K. E., Rasooly, A., Taitt, C. R., Ligler, F. S., 2004. Anal. Chem. 76, 433-440.

Soto, C. M., Srinivasan, A., Ratna, B. R., 2002. J. Am. Chem. Soc. 124, 8508-8509.

Storhoff, J. J., Mucic, R. C., Mirkin, C. A., 1997. J. Cluster Sci. 8, 179-216.

Strable E., Johnson, J. E., Finn, M. G., 2004. Nano Lett. 4, 1385-1389.

Wang, Q.; Lin, T., Johnson, J. E., Finn, M. G., 2002. Angew. Chem. Int. Ed. 41, 459-462.

What we claim:

1. A non-enveloped virus particle, comprising:
   (a) at least one analyte binding moiety attached to a capsid protein of the particle; and
   (b) a plurality of detectable fluorescent labels attached to capsid proteins of the particle;

wherein the detectable fluorescent labels are Cy5; and wherein the detectable fluorescent labels are sufficiently distanced from each other to prevent fluorescence quenching between neighboring detectable fluorescent labels.

2. A non-enveloped virus particle of claim 1, wherein said non-enveloped viral particle is cowpea mosaic virus that comprises at least one surface exposed cysteine which is not present in the naturally-occurring cowpea mosaic virus.

3. A non-enveloped virus particle of claim 1, wherein said non-enveloped viral particle is cowpea mosaic virus that comprises a mutation in its large subunit in which a cysteine is inserted between amino acid at position 98 and 99.

4. A non-enveloped virus particle of claim 3, furthering comprising an antibody, avidin or neutravidin at lysine-38 of its small subunit.

5. A non-enveloped virus particle of claim 1, wherein said non-enveloped viral particle is cowpea mosaic virus that comprises mutations in its large subunit in which the amino acids at positions 28 and 102 are substituted with cysteines.

6. A method of identifying the presence of an analyte, comprising:

contacting said analyte with a non-enveloped viral particle comprising:

(a) at least one analyte binding moiety attached to a capsid protein of the viral particle; and (b) a plurality of detectable fluorescent labels attached to capsid proteins of the particle, under conditions effective for the analyte binding moiety to bind to the analyte, wherein the detectable fluorescent labels are Cy5; and wherein the detectable fluorescent labels are sufficiently distanced from each other to prevent fluorescence quenching between neighboring detectable fluorescent labels; and detecting the fluorescence of said viral particle when bound to said analyte, wherein the presence of said analyte is identified.

7. A method of claim 6, wherein the viral particle comprises the viral genome.

8. A method of claim 6, wherein the viral particle lacks the viral genome.

9. A method of claim 6, wherein said non-enveloped viral particle is cowpea mosaic virus that comprises a mutation in its large subunit in which a cysteine is inserted between amino acid at position 98 and 99.

10. A method of claim 9, furthering comprising an antibody, avidin or neutravidin at lysine-38 of its small subunit.

11. A method of claim 6, wherein said non-enveloped viral particle is cowpea mosaic virus that comprises mutations in its large subunit in which the amino acids at positions 28 and 102 are substituted with cysteines.

12. A method of claim 6, wherein said analyte is a DNA or RNA.

13. A method of claim 6, wherein said analyte is a polypeptide.

14. A method of claim 12, wherein said DNA or RNA is present on a microarray.

15. A method of claim 13, wherein said analyte is present in a cell or tissue section which is deposited on a substrate.

16. A method of claim 6, wherein said non-enveloped viral particle is cowpea mosaic virus that comprises a mutation in its large subunit in which a cysteine is inserted between amino acid at position 98 and 99.

17. A method of detecting a target polynucleotide comprising,
- contacting a target polynucleotide in a test sample with a polynucleotide probe comprising a hapten under conditions effective to form a hybrid between said probe and target,
- contacting said hybrid with a viral particle of claim 1, and
- detecting the fluorescence of said viral particle when bound to said polynucleotide,
  - wherein the presence of said polynucleotide is identified and
  - wherein the hapten is an analyte which is specifically recognized by the by the analyte biding moiety of the viral particle.

18. A method of claim 17, wherein said target polynucleotide is bound to a solid phase.

19. A method of claim 18, wherein said solid phase is a DNA microarray.

20. A method of detecting a target polypeptide comprising,
- contacting a target polypeptide in a test sample with a polypeptide probe under conditions effective for said target to bind to said probe to form a target-probe complex,
- contacting said complex with a viral particle of claim 1, wherein said viral particle comprises an analyte binding moiety which specifically recognizes said target polypeptide, and
- detecting the fluorescence of said viral particle when bound to said complex,
  - wherein the presence of said target is identified.

21. A non-enveloped virus particle of claim 1, wherein said non-enveloped viral particle is a cowpea mosaic virus.

22. A method of claim 6, wherein said non-enveloped viral particle is a cowpea mosaic virus.

* * * * *